United States Patent [19]

Woker et al.

[11] Patent Number: 5,163,927
[45] Date of Patent: Nov. 17, 1992

[54] LINEAR EVERSION CATHETER SYSTEM WITH POSITION INDICATING INDICIA

[75] Inventors: Gary Woker, Escondido; Keith Tholin, Irvine; Stanley L. Van Gent, San Clemente, all of Calif.

[73] Assignee: Imagyn Medical, Inc., Laguna Niguel, Calif.

[21] Appl. No.: 780,095

[22] Filed: Oct. 17, 1991

[51] Int. Cl.[5] .............................................. A61M 5/00
[52] U.S. Cl. ...................................... 604/271; 604/53; 604/96
[58] Field of Search ................. 604/53, 96, 103, 117, 604/264, 271; 606/191; 128/772, 656, 657, 658

[56] References Cited

U.S. PATENT DOCUMENTS

| | | | |
|---|---|---|---|
| 4,559,046 | 12/1985 | Groshong et al. | 604/282 |
| 4,606,347 | 8/1986 | Fogarty et al. | 604/271 X |
| 4,838,879 | 6/1989 | Tanabe et al. | 604/280 |
| 4,863,440 | 9/1989 | Chin | 604/271 |
| 4,871,358 | 10/1989 | Gold | 604/271 |
| 4,990,138 | 2/1991 | Bacich et al. | 604/96 |

FOREIGN PATENT DOCUMENTS 0017777 10/1980 European Pat. Off. ............ 604/271
2406823 8/1975 Fed. Rep. of Germany ...... 604/271

OTHER PUBLICATIONS

"Hysterosalpingography & Selective Salpingography", Cook OB/GYN, A Division of Cook Urological Inc., p. 7, 1988.

Primary Examiner—John D. Yasko
Assistant Examiner—C. Maglione
Attorney, Agent, or Firm—Gordon L. Peterson

[57] ABSTRACT

An everting catheter system comprising an outer tube having an outer catheter lumen and an opening leading from the outer catheter lumen, an inner catheter movable longitudinally in the outer catheter lumen and having an inner catheter lumen and an everting element coupled to the outer catheter and the inner catheter so that with movement of the inner catheter distally in the outer catheter lumen, the everting element can be everted through the opening. An elongated instrument is movable longitudinally in the inner catheter lumen relative to the inner catheter. Indicia are provided on the inner catheter and the instrument for indicating at least one longitudinal position of the instrument relative to the distal end of the everting element.

22 Claims, 3 Drawing Sheets

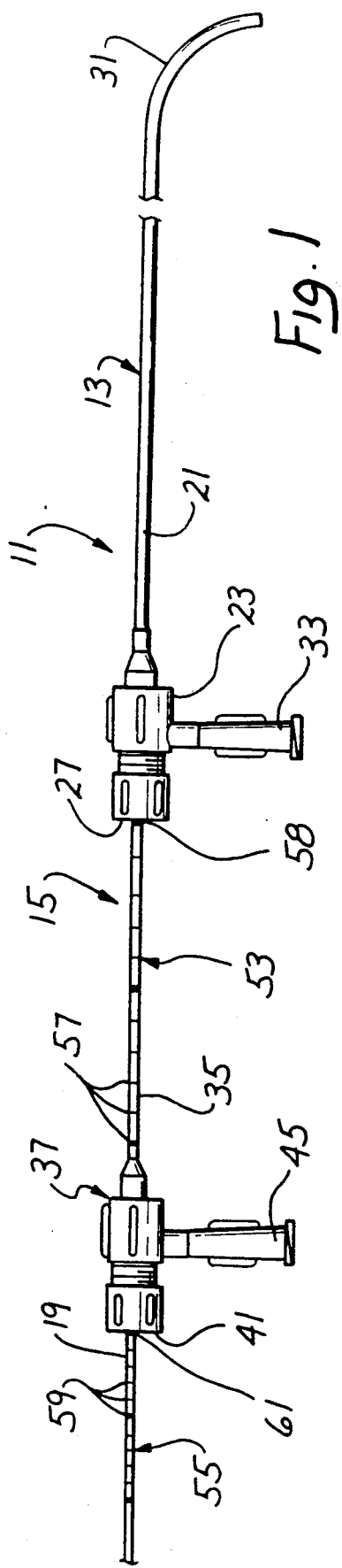
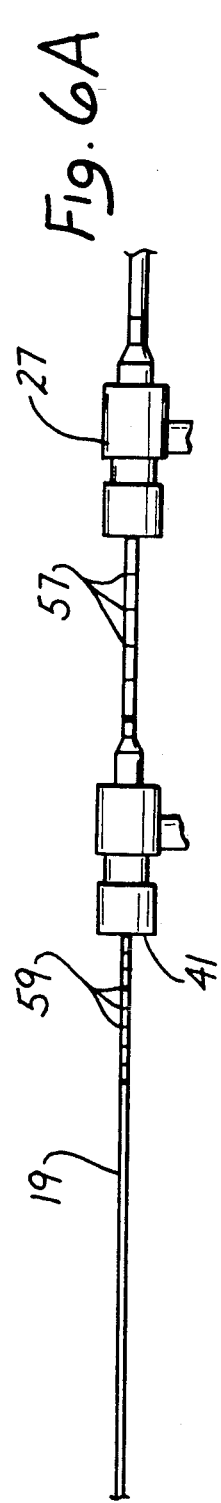
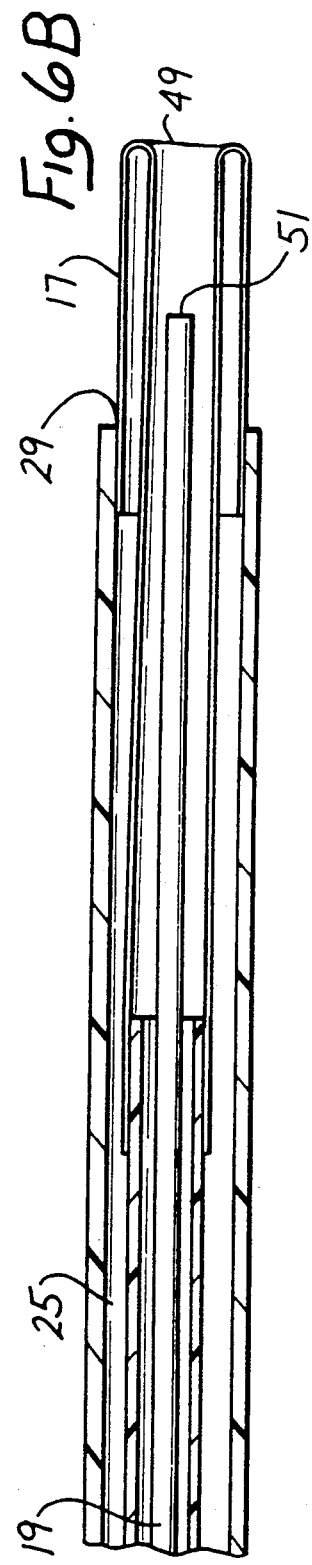

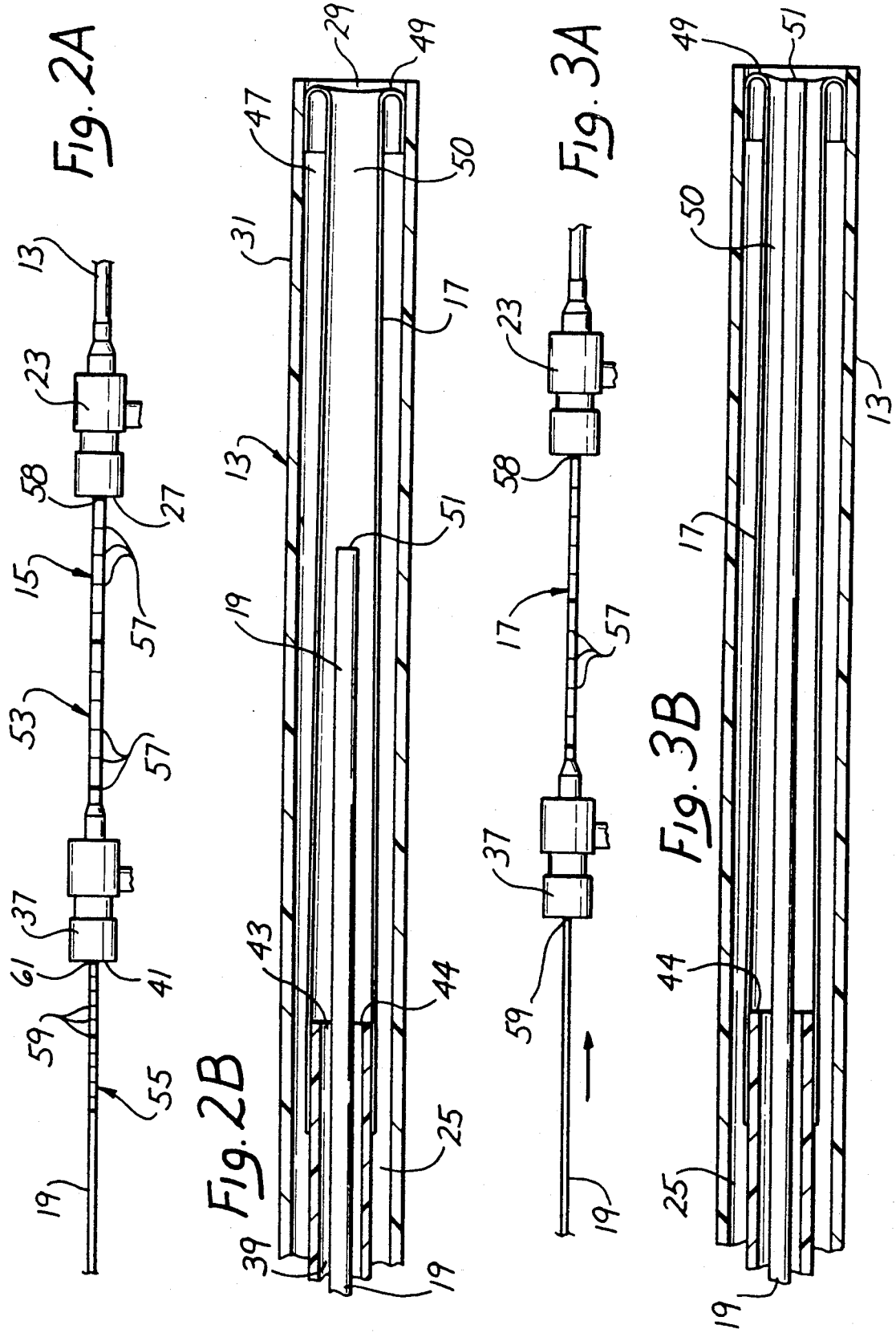

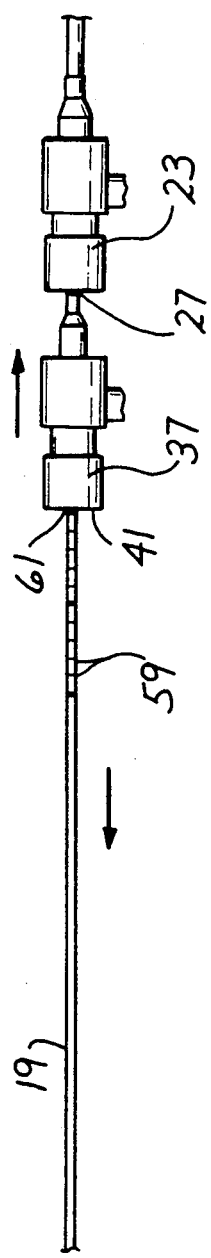
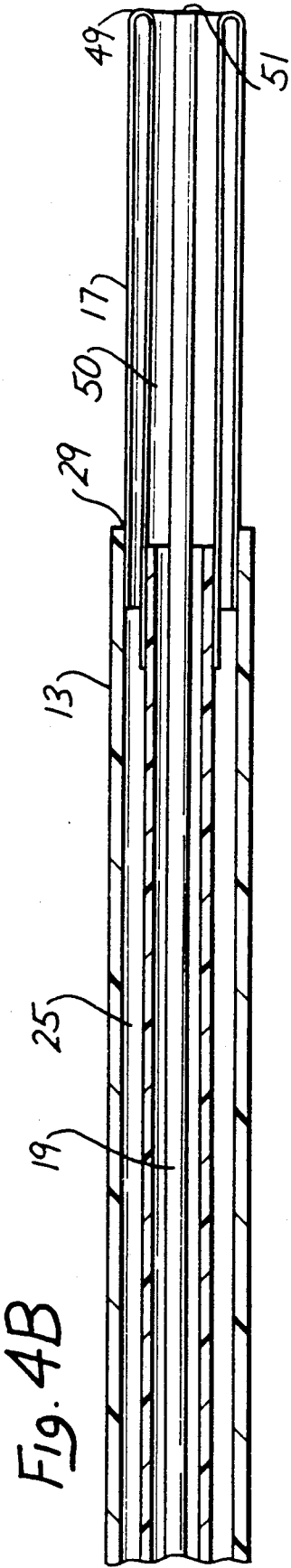
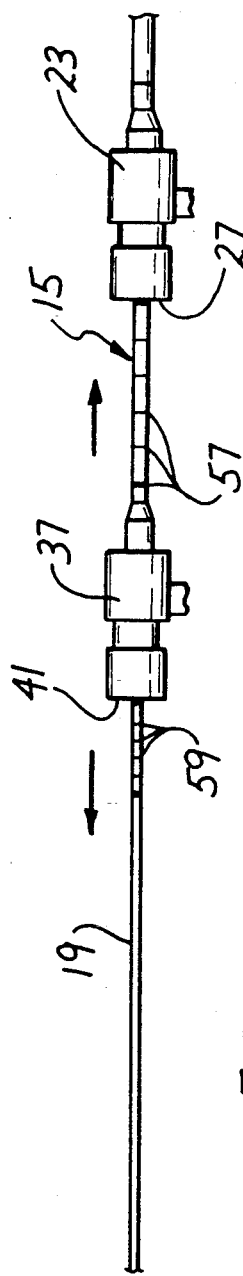
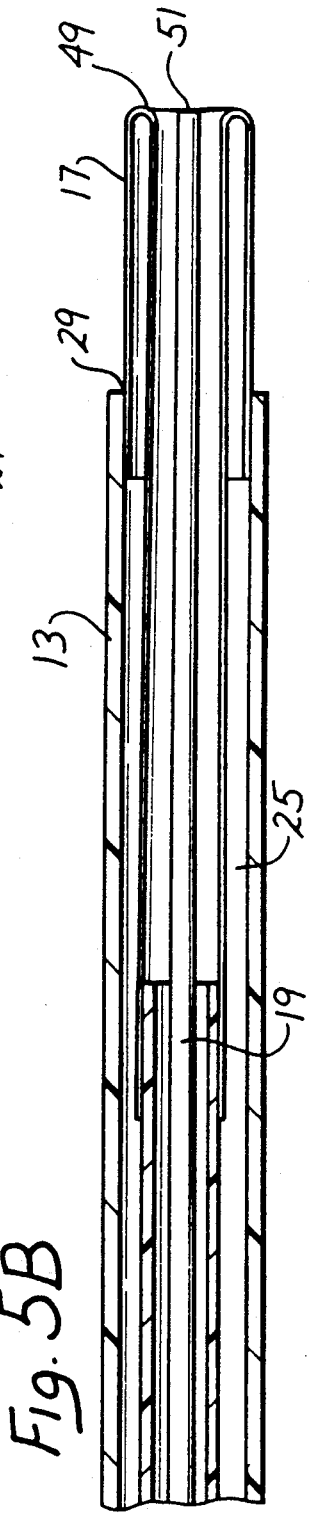

LINEAR EVERSION CATHETER SYSTEM WITH POSITION INDICATING INDICIA

BACKGROUND OF THE INVENTION

An everting catheter typically includes an outer catheter having an outer catheter lumen and an inner catheter movable longitudinally in the outer catheter lumen and having an inner catheter lumen. An everting element is coupled to the outer catheter and the inner catheter so that, with movement of the inner catheter distally in the outer catheter lumen, the everting element can be everted through an opening in the outer catheter.

An everting catheter of this type can be inserted through a passage in the human body with the everting element in an inverted position. An elongated, flexible instrument can then be introduced through the inner catheter lumen and the everted everting element to position the instrument into a desired body region and accomplish any of a variety of medical procedures and/or viewing of internal body regions.

In order that any of these functions can be properly carried out, it is commonly necessary to know the location of the distal end of the instrument in relation to the distal end of the everting element. This may be necessary, for example, to prevent the instrument from extending distally beyond the everting element where the instrument might cause injury to delicate body tissues or organs.

Prior art techniques for ascertaining the position of the instrument in relation to the distal end of the everting element include ultrasound and fluoroscopy. Unfortunately, neither of these techniques is satisfactory for use in the fallopian tubes. More specifically, ultrasound is uncomfortable for the patient and does not locate the distal end of the instrument in relation to the distal end of the everting element as precisely as desired. In this regard, it is important that the instrument not extend beyond the distal end of the everting element because of the very delicate nature of the fallopian tubes. Fluoroscopy is also not suitable because of the possibility that the X-rays will be detrimental to the patient's fertility.

SUMMARY OF THE INVENTION

This invention provides an everting catheter system which solves these problems. With this invention, the instrument can be accurately located relative to the distal end of the everting element, and this is accomplished without the need for relatively expensive position-detecting equipment, such as ultrasound or fluoroscopy equipment. In fact, the everting catheter system of this invention accomplishes the position-detecting function very inexpensively. Moreover, the position-detection technique of this invention is very easy to use and is unlikely to introduce error in ascertaining the position of the instrument relative to the distal end of the everting element.

Ascertaining the position of the distal end of the instrument relative to a distal opening in the outer catheter is relatively easy because the distal opening is typically fixed, and the instrument moves with respect to it. However, determining the relative position of the distal ends of the instrument and the everting element is more complex because the instrument and the everting element are independently movable. Moreover, because of the nature of an everting catheter, the distal end of the everting element moves only one-half as far as the inner catheter.

With this invention, indicia on the inner catheter and the instrument indicate at least one longitudinal position of the instrument relative to the distal end of the everting element. Preferably, the indicia indicate a plurality of longitudinal positions of the instrument relative to the distal end of the everting element, and these positions may be anywhere from the fully inverted position to the fully everted position. For use in the fallopian tubes, one important position that can be detected by this invention is when the distal end of the instrument is closely adjacent the distal end of the everting element, and this can be accomplished even when the everting element is between the fully inverted and fully everted positions.

In one preferred form, the indicia on the inner catheter are exposed to an extent which is related to the longitudinal position of the inner catheter in the outer catheter lumen, and the indicia on the instrument are exposed to an extent which is related to the longitudinal position of the instrument in the inner catheter lumen. With this arrangement, the longitudinal position of the instrument relative to the distal end of the everting element is related to the exposed indicia on both the inner catheter and the instrument. In addition, the indicia on the inner catheter indicate the position of the distal end of the everting element relative to the distal opening of the outer catheter so that the extent to which the everting element is everted is known.

Indicia have the advantage of being very inexpensive and easy to use. In addition, indicia can accurately show the position of the instrument relative to the distal end of the everting element.

The indicia can be of any type that will accomplish this purpose. For example, the indicia may include numbers and even longitudinal stripes of varying width. However, to simplify the system and thereby minimize the likelihood for error that could cause patient injury, the indicia preferably include a first set of spaced apart marks on the inner catheter and a second set of spaced apart marks on the instrument. These marks may be provided in any form which is human or machine readable; however, because these procedures are normally carried out by hand, human readable marks are preferred.

Because the distal end of the everting element moves at only one half the rate of the inner catheter, the adjacent marks on the inner catheter are spaced apart a distance which is twice the distance that adjacent marks on the instrument are spaced apart. More specifically, the position of the distal end of the instrument relative to the distal end of the everting element can be expressed as a function $P = I + S - K$ where P is the distance between the distal ends of the instrument and the everting element, I is the number of the exposed marks of the inner catheter, S is the number of exposed marks of the instrument and K is a constant. K can be defined in different ways. For example in one particular kind of everting catheter, K may be equal to the number of exposed marks of the inner catheter when the everting element is fully inverted or the number of exposed marks on the instrument when the everting element is fully everted and the distal end of the instrument is substantially at the distal end of the everting element. K may also be the number of exposed marks on the instrument when the distal end of the instrument is within the extension of the inner catheter lumen defined by the everting element and is spaced from the distal opening of the outer catheter about one half the distance that the distal end of the inner catheter is spaced from the distal opening of the outer catheter, and the everting element is fully inverted. K may also equal one half the sum of the exposable marks of the first and second set of marks. Preferably, the number of exposable marks on the instrument equals the number of exposable marks on the inner catheter.

The indicia on the instrument also include a baseline indicator which, in the preferred embodiment, is also spaced a distance X from an adjacent mark of the set of marks on the instrument. The baseline indicator is used to define a 0 or baseline position and is not considered as a mark usable in $P=I+S-K$ formula. Thus, by placing the instrument at a location in the inner catheter lumen such that the baseline indicator is either barely visible or just hidden, the exposed marks can be counted, and this is regarded as a baseline or 0 position of the instrument. Although the baseline indicator can be eliminated if desired, its use is preferred so that the 0 or baseline position can be accurately established; however, the baseline indicator is not counted in determining the location of the instrument relative to the distal end of the everting element. The indicia on the inner catheter may also include a baseline indicator which is also not counted in the $P=I+S-K$ formula.

The 2-to-1 spacing of the marks on the inner catheter of the instrument is not essential. However, it greatly simplifies use of the catheter system in that the location of the distal end of the instrument relative to the distal end of the everting element can be determined by simply counting the total number of exposed marks. In the preferred system, K equals 10, and a total of 10 exposed marks, i.e. P=0, means that the distal end of the instrument is at, or closely adjacent, the distal end of the everting element.

If P is greater than 0, the distal end of the instrument is within the everting element, and if P is negative, the distal end of the instrument extends distally beyond the distal end of the everting element. Moreover, the numerical value of P indicates the number of units of spacing between the distal ends of the instrument and the everting element. For example, if the adjacent marks on the instrument are spaced apart 1 centimeter and the adjacent marks on the inner catheter are spaced apart 2 centimeters, then if P equals 3, the physician knows that the distal end of the instrument is within the everting element and spaced 3 centimeters proximally of the distal end of the everting element.

Of course, the condition of P equals 0 need not indicate that the distal end of the instrument is precisely at the distal end of the everting element, and to provide a safety factor, the P equals 0 condition may indicate that the distal end of the instrument is closely adjacent the distal end of the everting element and may be slightly within the everting element. In a broader sense, the P equals 0 condition may identify any desired or known orientation of the distal ends of the instrument and the everting element.

The instrument may be any elongated instrument for examination of an interior body region or for carrying out a medical procedure on an interior body region. This invention is particularly adapted for use with a scope which enables interior body regions to be seen and which should not extend significantly or at all distally of the distal end of the everting element; however, this invention is not limited to this particular kind of instrument.

The invention, together with additional features and advantages thereof may best be understood by reference to the following description taken in connection with the accompanying illustrative drawing.

BRIEF DESCRIPTION OF THE DRAWINGS

FIG. 1 is a plan view illustrating one form of catheter system constructed in accordance with the teachings of this invention with the everting element inverted.

FIG. 2A is a fragmentary plan view of the catheter system illustrating a preferred form of indicia and with the everting element in the fully inverted position.

FIG. 2B is an enlarged, fragmentary, longitudinal sectional view of a distal region of the catheter system showing the positions of the distal end of the instrument and the distal end of the everting element which correspond to the positions of the instrument and inner catheter shown in FIG. 2A. For simplicity, the distal region of the catheter system is shown linear rather than curved.

FIGS. 3A, 4A, 5A and 6A are views similar to FIG. 2A showing different relative positions of the inner catheter and instrument, and FIGS. 3B, 4B, 5B and 6B are sectional views similar to FIG. 2B illustrating the positions of the distal ends of the instrument and everting element corresponding to FIGS. 3A, 4A, 5A and 6A, respectively. For simplicity of illustration, the everting element is not shown as inflated into gripping contact with the instrument.

DESCRIPTION OF THE PREFERRED EMBODIMENT

FIG. 1 shows a catheter system 11 which is particularly adapted for accessing the fallopian tubes; however, it should be understood that the features of this invention are also applicable to catheter systems adapted for other purposes. The catheter system 11 generally comprises an outer catheter 13, and inner catheter 15, an everting element 17 (FIG. 2B) and an elongated instrument 19. The outer catheter 13 includes an elongated, flexible catheter body 21 and an outer catheter fitting 23 coupled to the proximal end of the catheter body 21. The outer catheter 13 has an outer catheter lumen 25 (FIG. 2B) which extends from a proximal opening 27, which is provided by the outer catheter fitting 23 to a distal opening 29 (FIG. 2B) which, in this embodiment, is at the distal end of the catheter body 21. Of course, the catheter body 21 may have multiple lumens, if desired, and the distal opening 29 need not be at the distal end of the catheter body.

The catheter body 21 has a distal end portion 31 which, in its unstressed condition, may be straight or of any other shape designed to best gain access to a desired region of the body. As shown in FIG. 1, the distal end portion 31 is curved and forms a portion of a circular arc in the unstressed condition, and this facilitates access to the ostia of the fallopian tubes. However, the shape of the distal end portion 31 forms no part of this invention, and the distal end portion is shown for convenience in FIGS. 2B, 3B, 4B, 5B and 6B as linear.

The outer catheter 13 may be of conventional construction, and the catheter body 21 may be constructed of a flexible, biocompatible polymeric material. The outer catheter fitting 23 has an injection leg 33 through which an inflation media can be supplied to the outer catheter lumen 25 to control the inversion and eversion of the everting element 17 in a known manner.

The inner catheter 15 is extendible through the proximal opening 27 of the outer catheter 13 and is movable longitudinally in the outer catheter lumen 25. The inner catheter 15 also includes a catheter body 35 and an inner catheter fitting 37 coupled to the proximal end of the catheter body 35. The inner catheter 15 has an inner catheter lumen 39 (FIG. 2B) which extends between a proximal opening 41 provided by one leg of the inner catheter fitting 37 and a distal opening 43 (FIG. 2B) at the distal end 44 of the catheter body 35.

The catheter body 35 may be flexible or rigid depending upon the nature and purpose of the catheter system 11. However, in this embodiment, a distal region of the catheter body 35 is flexible such that the portion of the catheter body 35 that is within the distal end portion 31 in all positions of the inner catheter 15 relative to the outer catheter 13 is flexible.

The fitting 37 has an injection leg 45 which can be used, for example, for injecting irrigation fluid, a contrast dye or drugs into the inner catheter lumen 39. The leg 45 can also be used for aspiration, if desired.

The everting element 17 (FIG. 2B) is a thin, flexible membrane which is constructed of a suitable polymeric material. The everting element 17 is bonded as by an adhesive to the catheter body 21 of the outer catheter 13 closely adjacent the distal opening 29 and to a distal tip region of the catheter body 35 of the inner catheter 15 in accordance with known techniques. This forms a chamber 47 with the catheter body 21 of the outer catheter 13. Consequently, inflation media from the injection leg 33 acting in the chamber 47 can bring about inversion and eversion of the everting element 17. The everting element 17 has a distal end 49 which, in the position of FIG. 2B, is substantially at the distal opening 29. The everting element 17 forms an extension 50 of the inner catheter lumen 39.

The instrument 19 is elongated and flexible. The instrument 19 is introduced to the inner catheter lumen 39 through the proximal opening 41 and can be moved both proximally and distally relative to the inner catheter 15 independently of the inner catheter. The instrument 19 terminates distally in a distal end 51 (FIG. 2B). In this embodiment, the instrument 19 is an endoscope for examination of the fallopian tubes.

Because the everting element 17 is coupled at one end to the inner catheter 15, these two members move together during the inversion and eversion. However, because the everting element 17 forms a double layer as best shown in FIGS. 4B, 5B and 6B, the inner catheter 15 must move longitudinally for 2 centimeters for each centimeter of movement of the distal end 49. Accordingly, locating the distal end 51 of the instrument with respect to the distal end 49 of the everting element is complicated by two factors, i.e., these distal ends are movable independently of each other and the inner catheter 15 moves twice the distance of the distal end 49 of the everting element.

In order to be able to know the longitudinal position of the instrument 19 relative to the distal end 49 of the everting element 17, this invention provides indicia 53 and 55 on the inner catheter 15 and the instrument 19, respectively. The indicia 53 on the inner catheter 15 are exposed to an extent which is related to the longitudinal position of the inner catheter in the outer catheter lumen 25. The indicia 53 also indicate the position of the distal end 49 of the everting element 17 relative to the distal opening 29 of the outer catheter 13. Similarly, the indicia 55 are exposed to an extent which is related to the longitudinal position of the instrument 19 in the inner catheter lumen 39. As explained more fully below, the longitudinal position of the instrument 19 relative to the distal end 49 of the everting element 17 is related to the exposed indicia 53 and 55 on both the inner catheter 15 and the everting element 17.

The indicia 53 on the inner catheter 15 includes a first set of marks 57 and an optional baseline indicator 58, and the indicia 55 of the instrument 17 includes a second set of marks 59 and a preferred, but not essential, baseline indicator 61. Adjacent marks 57, as well as the baseline indicator 58 and the adjacent mark 57, are spaced apart by a distance 2X, and adjacent marks 59, as well as the baseline indicator 61 and the adjacent mark 59, are spaced apart by one half that amount, i.e., by a distance X. In this embodiment, there are a total of ten of the marks 57 and ten of the marks 59, and the distance X is 1 centimeter. Except for the indicia 53 and 55, the catheter system 11 may be conventional.

FIG. 2B shows the everting element 17 in the fully inverted position, and in that position, all 10 of the indicia 57 on the inner catheter 15 are exposed as shown in FIG. 2A with the baseline indicator 58 being located at the proximal opening 27 of the fitting 23. For an outer catheter 13 and an inner catheter 15 of the construction shown in FIG. 2B, the instrument 19 is within the extension 50 of the inner catheter lumen 39 and is spaced from the distal opening 29 of the outer catheter 13 about one half the distance that the distal end 44 of the inner catheter 15 is spaced from the distal opening 29. This relationship would not exist, if for example, the inner catheter 15 were longer so that the distal end 44 were located distally of the position shown in FIG. 2B. In this position, all 10 of the marks 59 are exposed, with the baseline indicator 61 being located at the proximal opening 41 of the fitting 37.

The location of the distal end 51 of the instrument 19 in relation to the distal end 49 of the everting element 17 can be ascertained from the formula $P = I + S - K$ where P is the distance between the distal ends 49 and 51, I is the number of exposed marks 57 of the inner catheter 15, S is the number of exposed marks 59 of the instrument 19 and K is a constant. In this embodiment, K is 10. Although this number and arrangement of the marks 57 and 59 are preferred, other numbers and spacings of marks can be employed, if desired. For example, by employing additional marks 59 distally of the baseline indicator 61, exact positions of the distal end 51 of the instrument 19 relative to the distal end 49 of the everting element 17 can be determined even if the instrument is moved proximally from the position shown in FIG. 2B. Exposable marks are the number of marks 57 and 59 which are visible with the inner catheter 15 and the instrument 19 in their most proximal positions. In this embodiment as referred to above, there are 10 of the marks 57 and 59. Exposed marks are the marks 57 and 59 which are visible and not at the proximal openings 27 or 41. The baseline indicators 58 and 61 are not considered as exposed or exposable marks.

Applying the above formula to FIGS. 2A and 2B, it can be seen that P equals 10 plus 10 minus 10 or 10. Accordingly, the distal end 51 of the instrument 19 is spaced 10 units proximally of the distal end 49 of the everting element 17 as shown in FIG. 2B. In this case, the units are centimeters, and so the spacing between the distal ends 49 and 51 is 10 centimeters.

In FIGS. 3A and 3B, the instrument 19 is moved proximally in the inner catheter lumen 39 so that the most proximal mark 59 is at the proximal opening 41, and so none of the marks 59 is exposed. In this position, the distal end 51 of the instrument is essentially in the plane occupied by the distal end 49 of the everting element 17. The inner catheter 15 is in the same position as in FIGS. 2A and 2B. Accordingly, by applying the formula above, it can be seen that 0 plus 10 minus 10 equals 0 which notifies the physician that the distal end 51 is at, or substantially at, the distal end 49.

In FIGS. 4A and 4B, the everting element 17 is everted out of the distal opening 29, and the inner catheter 15 is advanced such that the most proximal mark 57 is at the proximal opening 27, and so none of the marks 57 is exposed. The instrument 19 is also moved proximally such that the baseline indicator 61 is at the proximal opening 41, and 10 of the marks 59 are exposed as shown in FIGS. 4A. Applying the above formula, 10 plus 0 minus 10 equals 0 which again indicates to the physician that the distal end 51 of the instrument is at, or substantially at, the distal end 49 of the everting element 17. In the position of FIGS. 4A and 4B, the distal end 51 is at, or substantially at, the distal end 49, and K is equal to I, i.e. the number of exposed marks 59 on the instrument.

In FIGS. 5A and 5B, the everting element 17 is partially everted out of the distal opening 29, and the inner catheter 15 is positioned accordingly as shown in FIG. 5A such that the fifth mark 57 is at the proximal opening 27, and 5 of the marks 57 are exposed. Similarly, the instrument 19 is moved within the inner catheter lumen 39 such that 5 of the marks 59 are exposed. Applying the above formula, 5 plus 5 minus 10 equals 0 which again informs the physician that the distal end 51 of the instrument 19 is at, or substantially at, the distal end 49 of the everting element 17.

In FIGS. 6A and 6B, the inner catheter 15 is in the same position as in FIGS. 5A and 5B, and the everting element 17 is partially everted to the same extent as in FIGS. 5A and 5B so that 5 of the marks 57 are exposed. However, the instrument 19 is located proximally of the position it occupies in FIGS. 5A and 5B such that the distal end 51 is retracted from the distal end 49 as shown in FIG. 6B. Consequently, the second distal-most mark 59 is at the proximal opening 41, and there are 8 of the marks 59 exposed. Applying the formula, 8 plus 5 minus 10 equals 3 which informs the physician that the distal end 51 is located 3 centimeters proximally of the distal end 49.

Many other relative positions of the distal ends 49 and 51 can be determined utilizing the indicia 53 and 55, and the examples given above are purely illustrative. It should, however, be noted that, by moving the instrument 19 distally from the position shown in FIGS. 6A and 6B until the most proximal mark 59 is at the proximal opening 41 would cause the distal end 51 to protrude distally of the distal end 49. In this event, the physician would be informed by the fact that the formula would yield 0 plus 5 minus 10 equals −5 which is notification that the distal end 51 of the instrument 19 extends 5 centimeters beyond the distal end 49 of the everting element 17.

Although an exemplary embodiment of the invention has been shown and described, many changes, modifications and substitutions may be made by one having ordinary skill in the art without necessarily departing from the spirit and scope of this invention.

We claim:

1. An everting catheter system comprising:
    an outer catheter having proximal and distal ends an outer catheter lumen and an opening leading from said outer catheter lumen;
    an inner catheter movable longitudinally in the outer catheter lumen and having proximal and distal ends an inner catheter lumen;
    an everting element coupled to the outer catheter and the inner catheter so that with movement of the inner catheter distally in the outer catheter lumen the everting element can be everted through said opening, said everting element having a distal end;
    an elongated instrument movable longitudinally in the inner catheter lumen relative to the inner catheter; and
    indicia on the inner catheter and the instrument for indicating at least one longitudinal position of the instrument relative to the distal end of the everting element.

2. An everting catheter system as defined in claim 1 wherein the indicia indicate a plurality of the longitudinal positions of the instrument relative to the distal end of the everting element.

3. An everting catheter system as defined in claim 1 wherein the indicia indicate said one longitudinal position of the instrument when the everting element is partially everted.

4. An everting catheter system as defined in claim 1 wherein said indicia include a first set of spaced apart marks on the inner catheter and a second set of spaced apart marks on the instrument, the spacing between adjacent marks on the inner catheter being twice the spacing between adjacent marks on the instrument.

5. An everting catheter system as defined in claim 1 wherein the instrument has a distal end, the everting element has fully inverted and fully everted positions and said one longitudinal position occurs when the distal end of the instrument is closely adjacent the distal end of the everting element and the everting element is between the fully inverted and fully everted positions.

6. An everting catheter system as defined in claim 1 wherein the instrument includes a scope to enable interior body regions to be seen.

7. An everting catheter system as defined in claim 1 wherein the indicia on the inner catheter indicates the position of the distal end of the everting element relative to the opening of the outer catheter.

8. An everting catheter system comprising:
    an outer catheter having proximal and distal openings and an outer catheter lumen extending between the proximal and distal openings;
    an inner catheter extendible through the proximal opening of the outer catheter and movable longitudinally in the outer catheter lumen, said inner catheter having proximal and distal openings and an inner catheter lumen extending between the proximal and distal openings of the inner catheter;
    an everting element coupled to the outer catheter and the inner catheter so that with movement of the inner catheter distally in the outer catheter lumen the everting element can be everted through said distal opening of the outer catheter and form an extension of the inner catheter lumen, said everting element having a distal end;
    an elongated instrument movable longitudinally in the inner catheter lumen relative to the inner catheter and being extendible through the proximal opening of the inner catheter; and the inner catheter having indicia which are exposed to an extent which is related to the longitudinal position of the inner catheter in the outer catheter lumen, and the instrument having indicia which are exposed to an extent which is related to the longitudinal position of the instrument in the inner catheter lumen, the longitudinal position of the instrument relative to the distal end of the everting element being related to the exposed indicia on both of the inner catheter and the instrument.

9. A catheter system as defined in claim 8 wherein the indicia of the inner catheter include a first set of marks with adjacent marks spaced apart by a distance 2X and the indicia of the instrument include a second, set of marks with adjacent marks spaced apart by a distance X.

10. A catheter system as defined in claim 9 wherein the instrument has a distal end and the position of the distal end of the instrument relative to the distal end of the everting element is a function of $I+S-K$ where I is the number of exposed marks of the inner catheter, S is the number of exposed marks of the instrument and K is a constant.

11. A catheter system as defined in claim 10 wherein the everting element can be inverted and K is equal to the number of exposed marks of the inner catheter when the everting element is fully inverted.

12. A catheter system as defined in claim 11 wherein the inner catheter has a distal end and the instrument has K exposed marks when the distal end of the instrument is within the extension of the inner catheter lumen and is spaced from the distal opening of the outer catheter about one half the distance that the distal end of the inner catheter is spaced from the distal opening of the outer catheter and the everting element is fully inverted.

13. A catheter system as defined in claim 10 wherein K equals 10.

14. A catheter system as defined in claim 10 wherein there are 10 exposable marks on each of the inner catheter and the instrument.

15. A catheter system as defined in claim 10 wherein K equals one-half the sum of exposable marks of the first and second sets of marks.

16. A catheter system as defined in claim 10 wherein the instrument has a distal end and $K=I$ when the everting element is fully everted and the distal end of the instrument is substantially at the distal end of the everting element.

17. A catheter system as defined in claim 9 wherein the number of exposable marks on the instrument equals the number of exposable marks on the inner catheter.

18. A catheter system as defined in claim 9 wherein X equals 1 centimeter.

19. A catheter system as defined in claim 9 wherein the indicia on the instrument includes a baseline indicator which is spaced a distance X from an adjacent mark of the second set of marks.

20. A catheter system as defined in claim 8 wherein the indicia on the inner catheter include a plurality of marks which indicate the position of the distal end of the everting element relative to the distal opening of the outer catheter.

21. A method of ascertaining the longitudinal position of an elongated instrument relative to a distal end of an everting element of an everting catheter system wherein the everting catheter system includes an outer catheter having an outer catheter lumen and an opening leading from said outer catheter lumen, an inner catheter movable longitudinally in the outer catheter lumen and having an inner catheter lumen, and the everting element is coupled to the inner catheter and the outer catheter, and an instrument movable longitudinally in the outer catheter lumen relative to the outer catheter wherein there are indicia on the inner catheter and the instrument which are exposed to different degrees depending on the longitudinal positions of the inner catheter and the instrument, said method comprising:

observing the exposed indicia on the inner catheter and the instrument; and ascertaining from the exposed indicia the longitudinal position of the elongated instrument relative to the distal end of the everting element.

22. A method as defined in claim 21 wherein the indicia include a first set of spaced apart marks on the inner catheter and a second set of spaced apart marks on the instrument, the spacing between adjacent marks on the inner catheter being twice the spacing between adjacent marks on the instrument, and the step of ascertaining includes counting the total number of marks on the instrument and the inner catheter which are exposed.

* * * * *

UNITED STATES PATENT AND TRADEMARK OFFICE
CERTIFICATE OF CORRECTION

PATENT NO. : 5,163,927

DATED : November 17, 1992

INVENTOR(S) : Gary Woker et al

It is certified that error appears in the above-identified patent and that said Letters Patent is hereby corrected as shown below:

Column 10, line 28, after the "," insert -- and the inner catheter and the -- delete "an" before "instrument" and after "instrument" insert -- are -- .

Signed and Sealed this

Seventh Day of June, 1994

Attest:

BRUCE LEHMAN

Attesting Officer

Commissioner of Patents and Trademarks